US009989522B2

(12) United States Patent
Kristensen et al.

(10) Patent No.: US 9,989,522 B2
(45) Date of Patent: Jun. 5, 2018

(54) METHODS AND MATERIALS FOR MODULATING START-UP TIME AND AIR REMOVAL IN DRY SENSORS

(75) Inventors: Jesper Svenning Kristensen, Virum (DK); Tri T. Dang, Winnetka, CA (US); Katharine Knarreborg, Pasadena, CA (US); Anubhuti Bansal, Northridge, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 925 days.

(21) Appl. No.: 13/478,356

(22) Filed: May 23, 2012

(65) Prior Publication Data

US 2013/0109039 A1    May 2, 2013

Related U.S. Application Data

(60) Provisional application No. 61/554,057, filed on Nov. 1, 2011, provisional application No. 61/587,819, filed on Jan. 18, 2012.

(51) Int. Cl.
*C12Q 1/54* (2006.01)
*G01N 33/52* (2006.01)
(Continued)

(52) U.S. Cl.
CPC ........ *G01N 33/525* (2013.01); *A61B 5/145* (2013.01); *A61B 5/1455* (2013.01); *A61B 5/14532* (2013.01); *A61B 5/14865* (2013.01); *A61B 5/6861* (2013.01); *G01N 21/77* (2013.01); *G01N 33/487* (2013.01); *A61B 5/14556* (2013.01); *A61B 2562/02* (2013.01); *A61B 2562/028* (2013.01); *A61B 2562/162* (2013.01)

(58) Field of Classification Search
None
See application file for complete search history.

(56) References Cited

U.S. PATENT DOCUMENTS 4,755,173 A     7/1988  Konopka et al.
4,978,503 A *  12/1990  Shanks et al. ................ 422/412
(Continued)

FOREIGN PATENT DOCUMENTS

EP      0625704      11/1994
EP      1967847       9/2008
(Continued)

OTHER PUBLICATIONS

Ballerstadt et al., J. Diabetes Sci. Technol. 1(3): 384-393 (2007).*
(Continued)

*Primary Examiner* — Erin M. Bowers
(74) *Attorney, Agent, or Firm* — Gates & Cooper LLP

(57) ABSTRACT

The invention relates to sensors configured to include compositions disposed in specific regions of the sensor in order to provide the sensors with enhanced functional properties, for example faster start-up times. These compositions include, for example, hygroscopic compositions, gas generating compositions and gas solvating compositions. While typical embodiments of the invention pertain to glucose sensors, the systems, methods and materials disclosed herein can be adapted for use with a wide variety of sensors known in the art.

14 Claims, 13 Drawing Sheets

(51) Int. Cl.
  *G01N 33/487* (2006.01)
  *A61B 5/00* (2006.01)
  *A61B 5/145* (2006.01)
  *A61B 5/1455* (2006.01)
  *A61B 5/1486* (2006.01)
  *G01N 21/77* (2006.01)

(56) References Cited

U.S. PATENT DOCUMENTS

| | | |
|---|---|---|
| 5,391,250 A | 2/1995 | Cheney, II et al. |
| 5,485,408 A | 1/1996 | Blomquist |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 2003/0171666 A1 | 9/2003 | Loeb et al. |
| 2007/0123819 A1 | 5/2007 | Mernoe et al. |
| 2007/0227907 A1 | 10/2007 | Shah et al. |
| 2008/0188723 A1 | 8/2008 | Kristensen et al. |
| 2008/0218759 A1 | 9/2008 | Colvin et al. |
| 2009/0131773 A1 | 5/2009 | Struve et al. |
| 2009/0187084 A1 | 7/2009 | Kristensen et al. |
| 2009/0221891 A1 | 9/2009 | Yu et al. |
| 2010/0025238 A1 | 2/2010 | Gottlieb et al. |
| 2010/0160861 A1 | 6/2010 | Causey, III et al. |
| 2011/0152654 A1 | 6/2011 | Wang et al. |
| 2011/0319734 A1 | 12/2011 | Gottlieb et al. |

FOREIGN PATENT DOCUMENTS

| | | |
|---|---|---|
| JP | 2002-528190 | 9/2002 |
| WO | 0024455 | 5/2000 |
| WO | 2004034032 | 4/2004 |
| WO | 2004059281 | 7/2004 |
| WO | 2005033676 | 4/2005 |
| WO | 2006061207 A1 | 6/2006 |

OTHER PUBLICATIONS

Fischer, Cytometry Part A 77A: 805-810 (2010).*
Jhu, http://web.archive.org/web/20100607100404/http://web.jhu.edu/animalcare/procedures/rat.html, archived Jun. 7, 2010, accessed May 25, 2016.*
PCT International Search Report dated Feb. 21, 2013 for PCT Application No. PCT/US2012/062674.
Ballerstadt, Ralph et al., "Fiber-Coupled Fluorescence Affinity Sensor for 3-Day in Vivo Glucose Sensing", Journal of Diabetes Science and Technology, Diabetes Technology Society, May 1, 2007, pp. 384-393, vol. 1, No. 3, US.
Huang et al., "Kinetics and mechanistic analysis of an extremely rapid carbon dioxide fixation reaction", Proc Natl Acad Sci 2011, 108(4): 1222-1227.

* cited by examiner

FIGURE 2A1
| TIME | | COMMENT |
|---|---|---|
| 0 MIN | 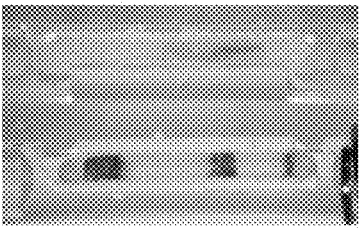 | SENSORS IN DRY STATE.<br><br>TOP SENSOR, ASSAY + NAHCO$_3$.<br><br>BOTTOM SENSOR; ASSAY + CA + SUCROSE + GALACTOSE + NH$_4$HCO$_3$ |
| 1 MIN |  | SENSORS IN WET CONDITION, 50 MM TRIS BUFFER SALINE PH 7.68, ROOM TEMPERATURE |
| 2 MIN |  | |
| 3 MIN |  | |
| 4 MIN | 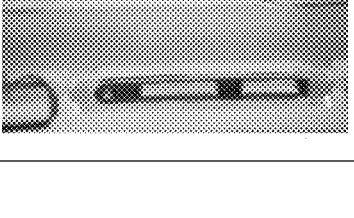 | |

FIGURE 2A2
| TIME | | COMMENT |
|---|---|---|
| 5 MIN | 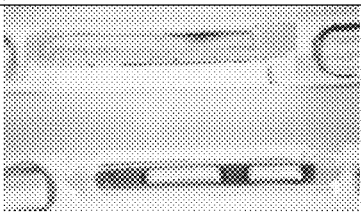 | |
| 10 MIN | 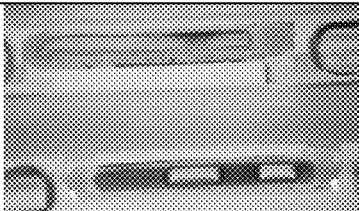 | |
| 15 MIN | 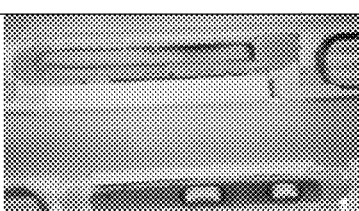 | |
| 21 MIN | 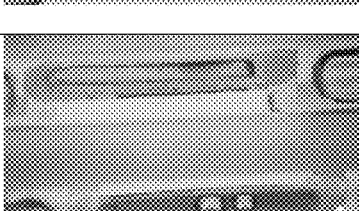 | |
| 27 MIN | 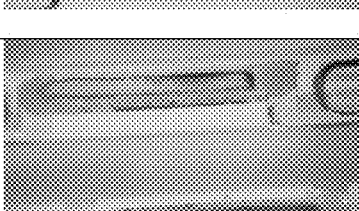 | |
| 32 MIN |  | FORMULATED SENSOR 90% FILLED |

FIGURE 2A3
| TIME | | COMMENT |
|---|---|---|
| 39 MIN | 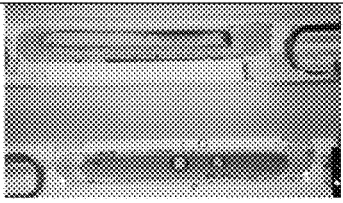 | |
| 50 MIN | 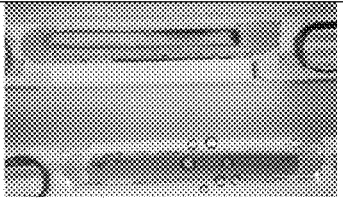 | |
| 61 MIN | 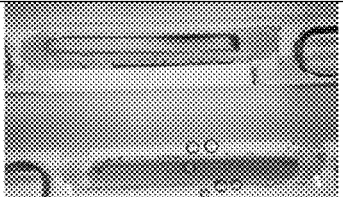 | |
| 72 MIN | 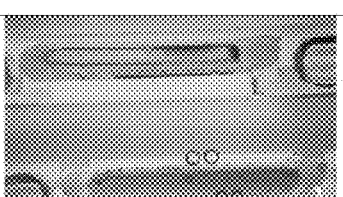 | |
| 83 MIN | 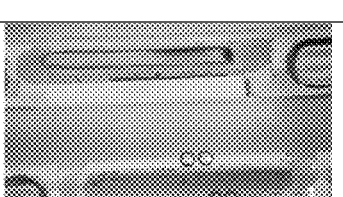 | UNFORMULATED SENSOR ONLY JUST WETTED INSIDE.<br><br>FORMULATED SENSOR COMPLETELY FILLED WITH LIQUID, NO AIR LEFT |

| No.: | Formulation | Under pressure: | 1/3 Full | 1/2 Full | 4/5 Full | 9/10 Full |
|---|---|---|---|---|---|---|
| 1 | NaHCO3 | yes | | | 3h | 72h |
| 2 | NaHCO3 | No directly on the freezedryer | | | 3h | 72h |
| 3 | PVA + Sucrose + NaHCO3 | yes | | 2h | | 72h |
| 4 | PVA + Sucrose | yes | | 2h | | 72h |
| 5 | PVA | yes | | | 2h | 72h |
| 6 | Tween80 + Sucrose | yes | | | 2h | 72h |
| 14 | Triton-X100 | yes | 2h | | | 72h |
| 15 | Sucrose + Trehalose | No directly on the freezedryer | | | 2h | |
| 16 | Sucrose + Trehalose | yes | | | | |
| 17 | Sucrose + Trehalose | No directly on the freezedryer | | | 2h | |
| 19 | Sucrose + Glucose | No directly on the freezedryer | | | 1h | 1h |
| 20 | Sucrose + Glucose | yes | | | 1h | 2h |
| 21 | Sucrose + Glucose | No directly on the freezedryer | | | | 1h |
| 22 | Sucrose + Glucose | yes | | | 1h | 2h |
| 24 | Lactose + Glucose | yes | | | 10 min | 1h |
| 25 | Glucose | yes | | | 2h | |

• Saccharide conc typical 0.5 M
• Surfactant conc typical 0.1%

FIG. 4

METHODS AND MATERIALS FOR MODULATING START-UP TIME AND AIR REMOVAL IN DRY SENSORS

CROSS REFERENCE TO RELATED APPLICATIONS

This application claims the benefit of U.S. provisional patent application No. 61/554,057 filed Nov. 1, 2011 and U.S. provisional patent application No. 61/587,819 filed Jan. 18, 2012, the entire contents of which are incorporated herein by reference.

BACKGROUND OF THE INVENTION

1. Field of the Invention

This invention relates to sensors useful in aqueous environments such as glucose sensors used in the management of diabetes.

2. Description of Related Art

Sensors are used to monitor a wide variety of compounds in different aqueous environments, including in vivo analytes. The quantitative determination of analytes in body fluids is of great importance in the diagnoses and maintenance of a number of pathological conditions. Illustrative analytes that are commonly monitored in a large number of individuals include glucose, lactate, cholesterol, and bilirubin. The determination of glucose concentrations in body fluids is of particular importance to diabetic individuals, individuals who must frequently check glucose levels in their body fluids to regulate the glucose intake in their diets. The results of such tests can be crucial in determining what, if any, insulin and/or other medication needs to be administered.

Analyte sensors typically include components that convert interactions with analytes into detectable signals that can be correlated with the concentrations of the analyte. For example, some glucose sensors use competitive binding assays, the readout of which is a detectable optical signal. These assays can include components such as glucose binding molecules coupled to elements (e.g. fluorophores) that generate different optical signals in the presence of glucose. Other glucose sensors use amperometric means to monitor glucose in vivo. Such amperometric glucose sensors typically incorporate electrodes coated with the glucose oxidase, an enzyme that catalyzes the reaction between glucose and oxygen to yield gluconic acid and hydrogen peroxide ($H_2O_2$). The $H_2O_2$ formed in this reaction then alters electrode current to form a detectable signal.

A number of sensors designed for use in aqueous environments are placed into a dry form following their manufacture in order to, for example, facilitate sensor sterilization and/or sensor packaging and/or sensor storage. In this context, methods and materials that facilitate the hydration of such dry sensors in aqueous environments, as well as other characteristics associated with sensor function in such environments, are desirable.

SUMMARY OF THE INVENTION

Embodiments of the invention provide sensor systems that include compositions disposed in specific regions of sensor architectures in order to provide sensors with enhanced functional and/or material properties, for example faster start-up times. Embodiments of the invention further provide methods for making and using such sensor systems. While typical embodiments of the invention pertain to glucose sensors, the systems, methods and materials disclosed herein can be adapted for use with a wide variety of sensors known in the art.

The invention disclosed herein has a number of embodiments. A typical embodiment of the invention is a sensor system comprising a sensor having an exterior surface and an internal matrix comprising at least one sensing complex adapted to sense analytes within aqueous environments. The sensor is substantially free of water prior to use, and includes a hygroscopic composition disposed on one or more parts of the sensor in order to effect certain functional characteristics. In particular, the hygroscopic composition is coupled to one or more regions of the sensor so as to modulate (e.g. increase) the rate of hydration of the sensing complex when the sensor is disposed within an aqueous environment. In this way, embodiments of the invention exhibit functional profiles (e.g. quicker start-up times) that are highly desirable to those using such systems (e.g. diabetic patients monitoring their physiological glucose concentrations). For example, in certain embodiments of the invention disclosed herein, the period of time between sensor contact with the aqueous environment (e.g. implantation in vivo) and generation of an observable analyte signal is less than 4, 3, 2 or 1 hours.

A number of aqueous analyte sensors are placed into a dry format in order to, for example, facilitate sensor sterilization and storage (e.g. in situations where a sensor is stored within a sealed, dry and sterile package environment). Processes involving the manufacture, packaging and storage of such sensors can result in the presence of air within the sensor, a phenomena that can, for example, increase the amount of time that the sensor must be disposed in an aqueous environment before the sensor is able to generate an observable analyte signal (e.g. one indicative of a concentration of blood glucose). In this context, certain embodiments of the invention comprise compositions designed to force air out of the sensors. In an illustrative embodiment of one such sensor system, the sensor includes a gas evolving composition coupled to one or more regions of the sensor and adapted to generate a gas (typically carbon dioxide) upon exposure to water (e.g. when the sensor is disposed within the aqueous environment) and in this way, displace the air so that it is forced out of the sensor. In certain embodiments of the invention disclosed herein, 90% of the air is forced out of the sensor in less than 4, 3, 2 or 1 hours following sensor exposure to an aqueous environment.

Typically the sensor system embodiments adapted to include a gas evolving composition also include a composition adapted to sequester, remove, solvate etc., the gas generated by the gas evolving composition. In an illustrative embodiment, the gas generated is carbon dioxide and the sensor system includes a carbonic anhydrase (CA) composition coupled to one or more regions of the sensor. In such embodiments, the carbonic anhydrase converts the carbon dioxide gas into soluble bicarbonates and protons that subsequently diffuse out of the sensor and into the aqueous environment. As discussed in detail below, the sensor systems of embodiments of the invention can include a number of other compositions, for example, those which can modulate sensor characteristics including those discussed above such as hydration, gas generation and/or gas removal. In some embodiments of the invention, the sensor comprises an acidic composition or a basic composition coupled to one or more regions of the sensor and adapted to modulate the pH within the sensor when the sensor is disposed within the aqueous environment. In some embodiments of the invention, the sensor comprises a convection composition coupled to one or more regions of the sensor and adapted to generate convection within the sensor when the sensor is disposed within the aqueous environment.

The compositions used in embodiments of the invention exhibit a surprising degree of flexibility and versatility, characteristics which allow them to be adapted for use a wide variety of sensor structures. Optionally the sensor comprises a cylindrical structure in the form of a tubular capsule formed from a biocompatible polymer and having a diameter of less than 1 mm, less than 0.5 mm or less than 0.25 mm. In some embodiments of the invention, the internal matrix of a cylindrical sensor comprises one or more cavities, for example an encapsulated longitudinal cavity. In certain embodiments of the invention, the sensing complex, the hygroscopic composition, the gas evolving composition, the composition adapted to sequester, remove, solvate etc., the gas generated by the gas evolving composition, the convection composition and/or the pH modulating composition is disposed in the one or more of these cavities.

In other embodiments of the invention, the sensor structure comprises planar layered elements and, for example, comprises a conductive layer including an electrode, an analyte sensing layer disposed over the conductive layer (e.g. one comprising glucose oxidase), and an analyte modulating layer disposed over the analyte sensing layer. In some embodiments of the invention, the hygroscopic composition is disposed within a planar layer (e.g. entrapped within a polymer of the layer), for example in the analyte sensing layer or the analyte modulating layer. In certain embodiments of the invention, the sensor electrode is disposed within a housing (e.g. a lumen of a catheter) and the hygroscopic composition coats a region of the housing. In one illustrative embodiment of the invention, the hygroscopic composition is entrapped within a composition disposed on an inner wall of a catheter lumen.

In many embodiments of the invention, the sensors comprise a biocompatible region adapted to be implanted in vivo. In some embodiments, an external sensor structure is formed from one or more biocompatible polymers (e.g. those that allow the diffusion of glucose therethrough) and is adapted to be completely implanted in vivo. In other embodiments, the sensor comprises a discreet probe that pierces an in vivo environment while other portions of the sensor remain in the external environment. In embodiments of the invention, the biocompatible region can comprise a polymer that contacts an in vivo tissue. Optionally, the polymer is a hydrophilic polymer (e.g. one that absorbs water). In this way, sensors used in the systems of the invention can be used to sense a wide variety of analytes in different aqueous environments. In common embodiments of the invention, the sensing complex is adapted to sense glucose.

A related embodiment of the invention is a method for modulating the time period between placement of a sensor within an aqueous environment and generation of a sensor signal that can be correlated with the concentration of a sensed analyte. The method comprises selecting the sensor to have an exterior surface and an internal matrix comprising at least one sensing complex adapted to sense analytes within aqueous environments; and a hygroscopic composition coupled to one or more regions of the sensor so as to modulate the rate of hydration of the sensing complex when the sensor is disposed within the aqueous environment (e.g. to increase the rate of hydration as compared to a control sensor that lacks the hygroscopic composition). This method further comprises placing the sensor into an aqueous environment where the hygroscopic composition influences hydration of the sensing complex. In such methods, the use and positional placement of the hygroscopic composition(s) within the sensors can be used to modulate the time period between: (1) sensor placement in the aqueous environment; and (2) generation of a sensor signal that can be correlated with the concentration of the analyte.

Certain methodological embodiments of the invention comprise forcing air out the internal matrix of a sensor (e.g. a cavity, such as one comprising the sensing complex), for example, by using a sensor that is formed to comprise a gas evolving composition coupled to one or more regions of the sensor, wherein the gas evolving composition is adapted to form carbon dioxide when the sensor is disposed within the aqueous environment, thereby forcing air out of the internal matrix of the sensor. Typically these methods include removing carbon dioxide atoms generated when the sensor is disposed within the aqueous environment, for example, by using a sensor that is formed to comprise carbonic anhydrase, allowing the carbonic anhydrase to convert the carbon dioxide into soluble bicarbonates and protons, and then allowing these molecules to diffuse out of the sensor into the aqueous environment. Some methodological embodiments of the invention comprise selecting and using sensors comprising compositions that provide other functional properties. For example, in some embodiments, the method comprises generating convection within the internal matrix of the sensor by using a sensor that is formed to comprise a convection composition, wherein the convection composition is coupled to one or more regions of the sensor so as to generate convection within the sensor (e.g. so as to facilitate mixing of other sensor constituents). Optionally, the convection composition comprises a hygroscopic composition. In addition, in some embodiments, the method comprises modulating a pH of a sensor region by using a sensor that is formed to include compositions that modulate pH in aqueous environments (e.g. buffering compounds, acid and basic compounds and the like).

Methodological embodiments of the invention can be used with sensors having a variety of configurations and/or sensing complexes. In certain methodological embodiments of the invention, the sensor comprises a cylindrical polymeric material having a diameter of less than 1 mm, less than 0.5 mm or less than 0.25 mm, the internal matrix comprises an encapsulated longitudinal cavity, and the sensing complex comprises a carbohydrate binding lectin (e.g. mannose binding lectin which binds glucose) coupled to one or more fluorophores. In other methodological embodiments of the invention, the sensor comprises an electrode coated with glucose oxidase and a glucose limiting membrane disposed over the glucose oxidase, wherein the glucose limiting membrane modulates the diffusion of glucose therethrough. In addition, methods of the invention can be performed in a variety of environments under conditions selected to be appropriate for a particular environment. For example, in certain embodiments of the invention, the aqueous environment comprises an in vivo tissue and the method is performed at a temperature between 36 and 38 degrees centigrade (e.g. human body temperature).

Embodiments of the invention also provide articles of manufacture and kits for observing a concentration of an analyte. In an illustrative embodiment, the kit includes a sensor comprising an exterior surface and an internal matrix comprising at least one sensing complex adapted to sense analytes within aqueous environments and one or more hygroscopic compositions. In illustrative embodiments of the invention, the hygroscopic composition can comprise a saccharide compound (e.g., a monosaccharide, an oligosaccharide etc.) and/or a polyol such as a polyvinyl alcohol or a polyethylene glycol, and/or a salt (e.g. one or more salts commonly used in pharmaceutical compositions). Optionally the sensor includes one or more gas (e.g. carbon dioxide) evolving compositions in combination with one or more gas removing compositions. In illustrative embodiments of the invention, the gas evolving composition comprises a compound selected from the group consisting of $NaHCO_3$, $Na_2CO_3$, $NH_4HCO_3$, $(NH_4)_2CO_3$, $KHCO_3$ and $K_2CO_3$, and a carbon dioxide gas removing composition comprises a composition selected from the group consisting of carbonic anhydrase and carbonic anhydrase analogues. In some embodiments, the sensing complex comprises a carbohydrate binding lectin coupled to a fluorophore. Alternatively, the sensing complex comprises an electrode coated with a glucose oxidase composition. In some embodiments, the sensors are disposed in the kit within a sealed, sterile, dry package that is impermeable to $CO_2$.

Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

BRIEF DESCRIPTION OF THE FIGURES

FIG. 2A provide a series of photographs taken over time of two freeze dried tubular capsule sensors that were immersed into Tris buffer (50 mM) at room temperature. As shown in these photographs, hygroscopic, $CO_2$ gas evolving and $CO_2$ gas solvating compositions can be used to modulate hydration as well as eliminate air from sensors immersed in an aqueous environment. The two sensors in these photographs are: Top sensor: sensors designated "S279" and formed from a cylindrical polymeric material having longitudinal cavity in which the compositions are disposed, in addition to a sensing complex. In particular, the top sensor comprises a cavity that includes a glucose sensing complex and 0.2 M NaHCO. The bottom sensor: is a S297 sensor comprising a glucose sensing complex as well as CA, 0.2 M NH4HCO3, 0.5M Sucrose and 0.5M Galactose.

FIG. 4 provides a table of data which illustrates to artisans how various combinations of the compositions disclosed herein (as well as conditions such as pressure) can be used to control the time required to fill a cavity/void space (e.g. one comprising a sensing complex) within a tubular capsule sensors. Combinations of compositions that fill this space in a relatively short period of time (and which therefore are useful in contexts where fast sensor start-up is desired) are circled.

DETAILED DESCRIPTION OF THE EMBODIMENTS

Figures 1A, 1B, 1C:
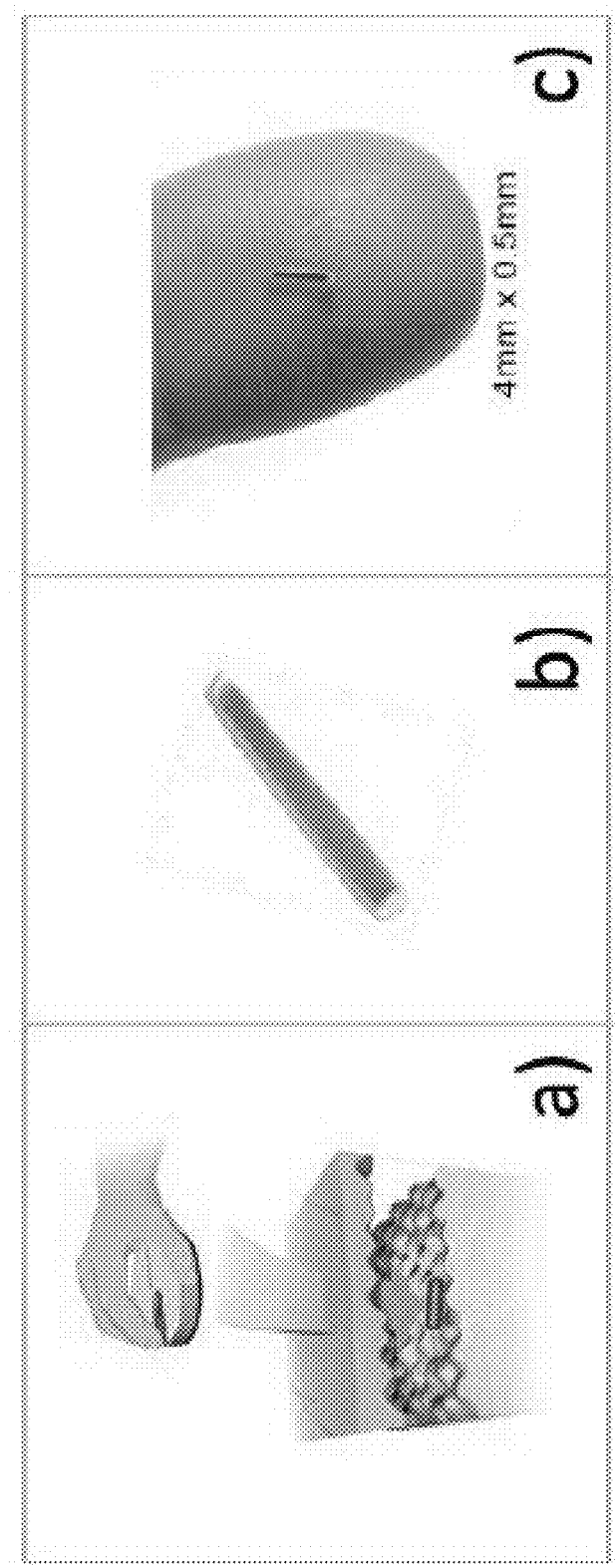
FIG. 1A shows a sensor design comprising a tubular capsule that is implanted under the skin and provides optical sensor in response to analyte (glucose).
FIG. 1B shows a view of this capsule.
FIG. 1C shows the relative size of this capsule.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted. A number of terms are defined below.

The term "analyte" as used herein is a broad term and is used in its ordinary sense, including, without limitation, to refer to a substance or chemical constituent in a fluid such as a biological fluid (for example, blood, interstitial fluid, cerebral spinal fluid, lymph fluid or urine) that can be analyzed. Analytes can include naturally occurring substances, artificial substances, metabolites, and/or reaction products. In common embodiments, the analyte is glucose. However, embodiments of the invention can be used with sensors designed for detecting a wide variety other analytes. Illustrative analytes include but are not limited to, lactate as well as salts, sugars, proteins fats, vitamins and hormones that naturally occur in vivo (e.g. in blood or interstitial fluids). The analyte can be naturally present in the biological fluid or endogenous; for example, a metabolic product, a hormone, an antigen, an antibody, and the like. Alternatively, the analyte can be introduced into the body or exogenous, for example, a contrast agent for imaging, a radioisotope, a chemical agent, a fluorocarbon-based synthetic blood, or a drug or pharmaceutical composition, including but not limited to insulin. The metabolic products of drugs and pharmaceutical compositions are also contemplated analytes.

The term "sensor" for example in "analyte sensor," is used in its ordinary sense, including, without limitation, means used to detect a compound such as an analyte. A "sensor system" includes, for example, elements, structures and architectures (e.g. specific 3-dimensional constellations of elements) designed to facilitate sensor use and function. Sensor systems can include, for example, compositions such as those having selected material properties, as well as electronic components such as elements and devices used in signal detection (e.g. optical detectors, current detectors, monitors, processors and the like). The term "sensing complex" as used herein refers to the elements of a sensor that interact with and generate a signal indicative of, a particular analyte (e.g. glucose and the like). The term "matrix" is used herein according to its art-accepted meaning of something within or from which something else is found, develops, and/or takes form.

As discussed in detail below, typical embodiments of the invention relate to the use of a sensor that measures a concentration of an aqueous analyte of interest or a substance indicative of the concentration or presence of the analyte in vivo. In some embodiments, the sensor is a subcutaneous, intramuscular, intraperitoneal, intravascular or transdermal device (e.g. is in the form of a capsule and/or fiber). Typically the sensor can be used for continuous analyte monitoring. In some embodiments, the device can analyze a plurality of intermittent blood samples. The sensor embodiments disclosed herein can use any known method, including invasive, minimally invasive, and non-invasive sensing techniques, to provide an output signal indicative of the concentration of the analyte of interest.

Embodiments of the invention disclosed herein provide sensors designed to include compositions disposed in specific areas of the sensor in order to provide the sensors with enhanced functional and/or material properties. The disclosure further provides methods for making and using such sensors. Embodiments of the invention described herein can be adapted and implemented with a wide variety of known sensors. Such sensors include, for example, those having sensing complexes that generate an optical signal that can be correlated with the concentration of an analyte such as glucose. A number of these sensors are disclosed, for example in U.S. Patent Application Publication Nos. 20080188723, 20090221891, 20090187084 and 20090131773, the contents of each of which are incorporated herein by reference. Embodiments of the invention described herein can also be adapted and implemented with amperometric sensor structures, for example those disclosed in U.S. Patent Application Publication Nos. 20070227907, 20100025238, 20110319734 and 20110152654, the contents of each of which are incorporated herein by reference.

A number of aqueous analyte sensors are placed into a dry format in order to, for example, facilitate sensor sterilization and storage (e.g. in situations where a sensor is stored within a sealed, dry and sterile package environment). In addition to being dry, processes involving the manufacture, packaging and storage of such sensors can result in the presence of air within the sensor, a phenomena that can, for example, increase the amount of time that the sensor must be disposed in an aqueous environment before the sensor is able to generate an observable analyte signal (e.g. one indicative of a concentration of blood glucose). The air inside certain sensor designs can take days to remove if the sensor is simply immersed into a buffer of the same osmotic pressure as a buffer inside the sensor.

Certain conditions can be applied to such sensors to facilitate air removal by increasing a rate of hydration and/or gas solubility and/or the dissolution of entrapped gases (e.g. air). Conditions include lowered temperatures, which are known to increase the gas solubility in general, as well as increased pressures (increased pressures increase gas solubility a characterized by according to Henry's law). However, the manipulation of these conditions is not always compatible with sensor use in certain contexts, for example in certain uses in vivo. For example with in vivo sensors (e.g. glucose sensors), a desirable start-up time would entail air removal within an hour or less, without cooling the sensor or pressurizing the sensor during the startup procedure. In addition, in certain contexts, it is desirable that dry sensors be used, as compared, for example to semi-filled wet sensors. Unfortunately, the dry state places even larger demands on solutions into which a sensor is placed. It is highly desirable to be able to both wet a sensor, and while wetting, remove air from inside the sensor. In many desirable contexts, such processes should be able to occur inside the body of a patient i.e. at relatively high temperatures.

The invention disclosed herein is designed to meet such challenges and the instant disclosure provides a number of working embodiments for doing so. A typical embodiment of the invention is a sensor system comprising a sensor having an exterior surface and an internal matrix comprising at least one sensing complex adapted to sense analytes within aqueous environments. The sensor in this system is substantially free of water prior to use, and includes compositions disposed on one or more parts of the sensor in order to effect certain desirable functional characteristics.

In certain embodiments of the invention, one or more hygroscopic compositions can be coupled to one or more regions of a sensor so as to modulate (e.g. increase) the rate of hydration of the sensing complex when the sensor is disposed within an aqueous environment. The term "coupled" as used in this context, means localization of the composition to a defined area (e.g. one comprising a sensing complex), either temporarily, or permanently. Compositions can be coupled to a defined area in a variety of ways. Illustrative, but non limiting ways in which a composition can be coupled to an area include, for example, disposing a composition within an enclosed void or cavity (see, e.g. the working example) and/or otherwise disposing a composition within a material (e.g. within a polymer matrix) and/or coating a surface of a material with a composition etc.

As used herein, "hygroscopic compositions" comprise those materials that can draw water into an area. As disclosed herein, the wetting of sensors can be greatly enhanced by formulating the sensor using hygroscopic compositions. A wide variety of hygroscopic compositions are known in the art which can be adapted for use with embodiments of the invention. The working embodiments of the sensors disclosed herein use various salts and sugars as well as polyols such as poly vinyl alcohol (PVA). In certain embodiments of the invention, the hygroscopic composition comprises combinations of monosaccharides (e.g. glucose) and disaccharides (e.g. sucrose, lactose and the like).

Hygroscopic compositions useful in embodiments of the invention can include, but are not limited to, these carbohydrates including monosaccharides, disaccharides and polysaccharides. These include monosaccharides such as glucose, dextrose (anhydrous and monohydrate), galactose, mannitol, D-mannose, sorbitol, sorbose and the like; disaccharides such as lactose, maltose, sucrose, trehalose, and the like; trisaccharides such as raffinose and the like; and other carbohydrates such as starches (hydroxyethylstarch), cyclodextrins, maltodextrins and hyaluronic acid. Hygroscopic compositions can also include salts such as one or more pharmaceutically acceptable salts, for example those disclosed in Remington: The Science and Practice of Pharmacy, University of the Sciences in Philadelphia (Ed), 21$^{st}$ Edition (2005). In some embodiments of the invention, a hygroscopic composition comprises a salt selected from the group consisting of sodium chloride, potassium chloride calcium chloride, magnesium chloride, zinc chloride, potassium carbonate, potassium phosphate, carnallite, ferric ammonium citrate, potassium hydroxide, and sodium hydroxide.

As noted above, depending upon the sensor structure and function desired, hygroscopic compositions useful with the invention can include a wide variety of combinations of sugars, salts, water soluble electrolytes, small organic compounds, and osmotic adjusting compositions to increase the osmotic pressure within an area and attract water. Other examples of hygroscopic compositions include polyethylene glycols, microcrystalline cellulose (AVICEL PH 200, AVICEL PH 101), Ac-Di-Sol (Croscarmelose Sodium) and PVP-XL (a crosslinked polyvinylpyrrolidone), starches and modified starches, polymers, and gum such as arabic and xanthan, and hydroxyalkyl cellulose such as hydroxymethylcellulose, hydroxypropylcellulose and hydroxyopropylmethylcellulose. Certain hygroscopic compositions of the invention include hydrogels (highly absorbent natural or synthetic polymers) such as those constructed from networks of biocompatible polymers, such as poly(ethylene glycols).

Figure 2B:
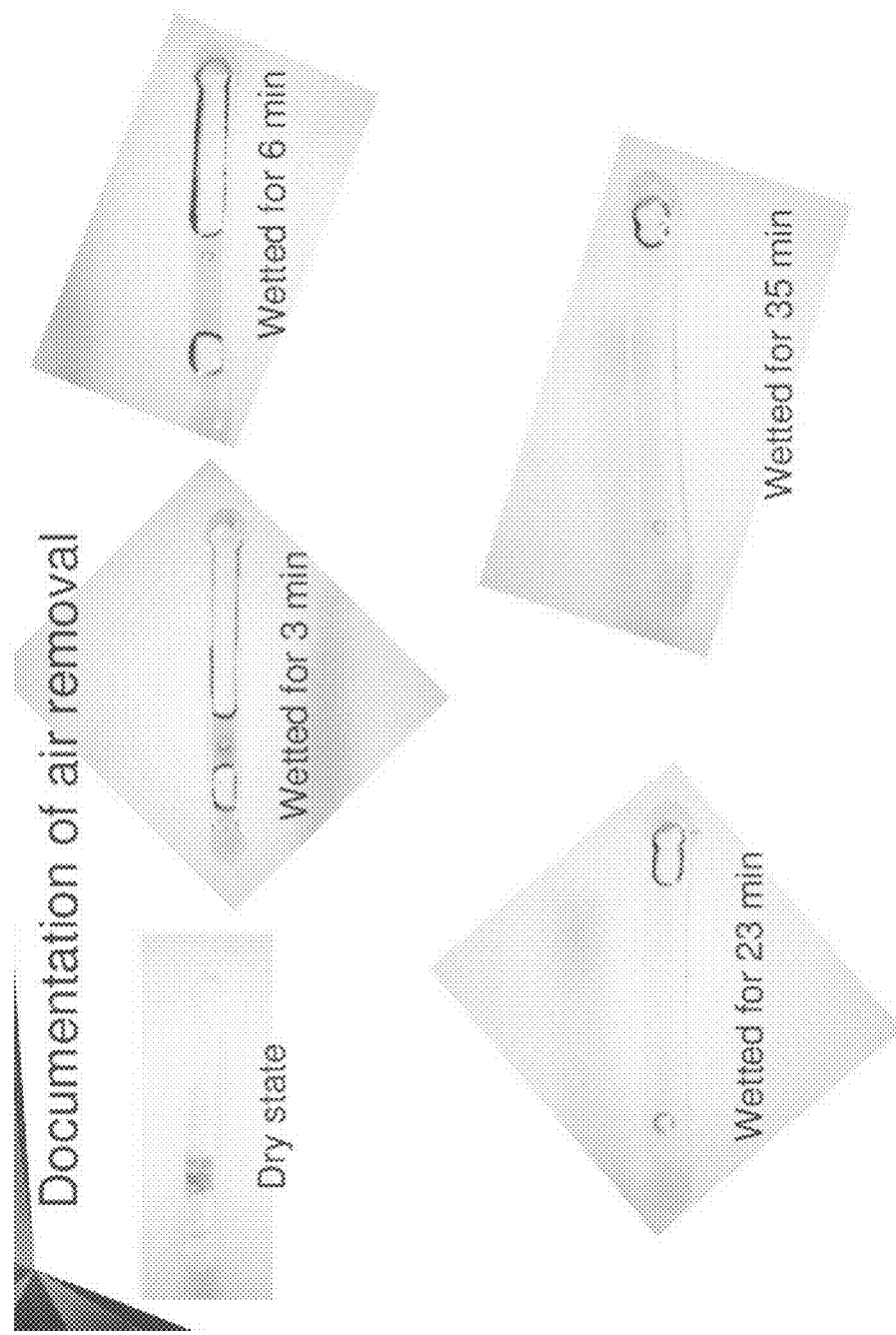
FIG. 2B provides a series of photographs taken over time of a freeze dried tubular capsule sensor having a selected combination of hygroscopic, $CO_2$ generating and $CO_2$ solvating compositions (see, e.g. Table 1 below) that has been immersed in aqueous environments.
Figure 3A:
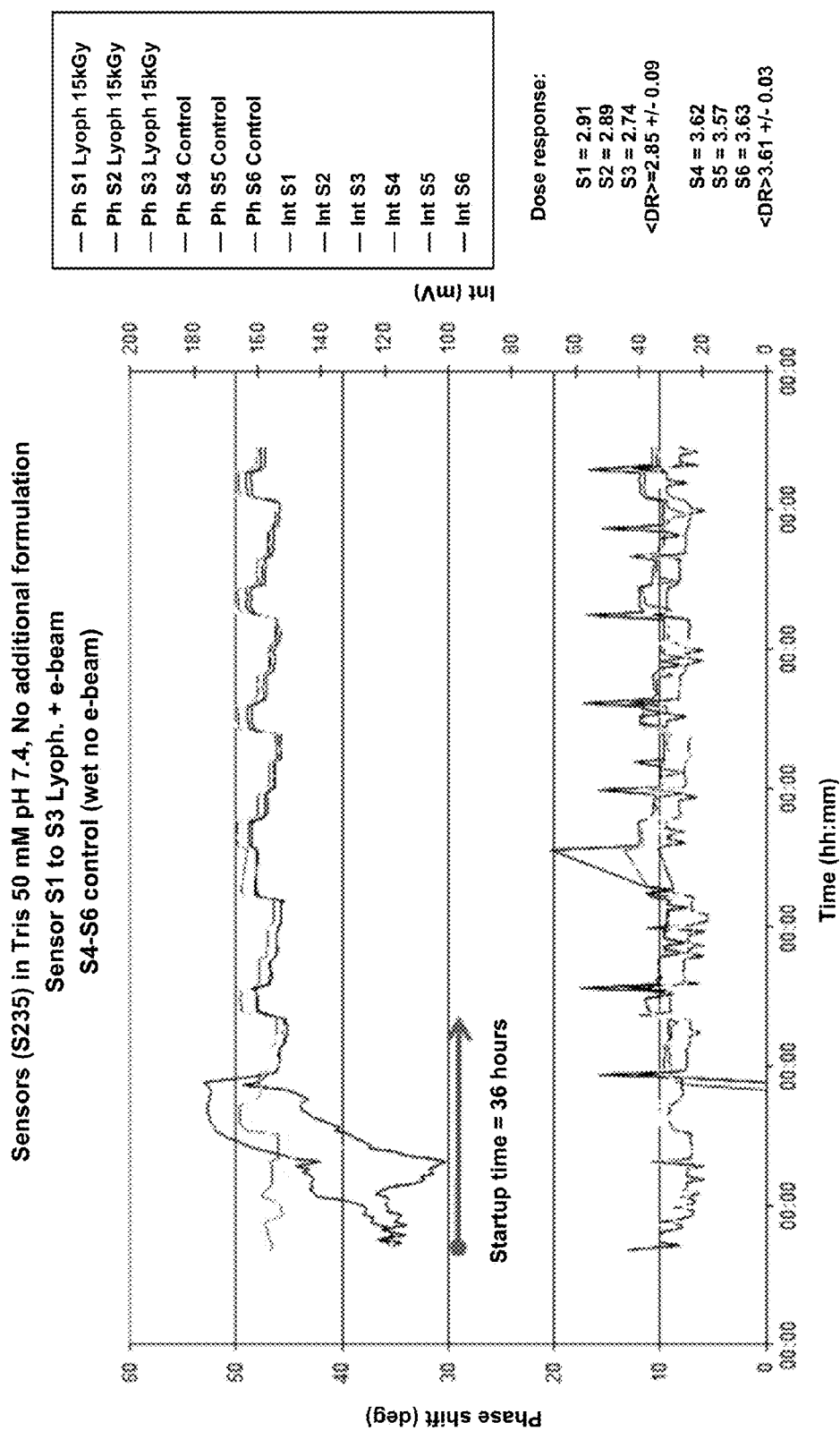
FIG. 3A provides a graph of data illustrating the startup of a freeze dried tubular capsule sensors lacking hygroscopic compounds in an in vitro setup. The top curves show the response from three wet sensors and three dry sensors. As seen the sensor startup of the dry sensors is much longer than the already filled wet sensors. The startup time of the dry sensors is found to be approximately 36 hours.
Figure 3B:
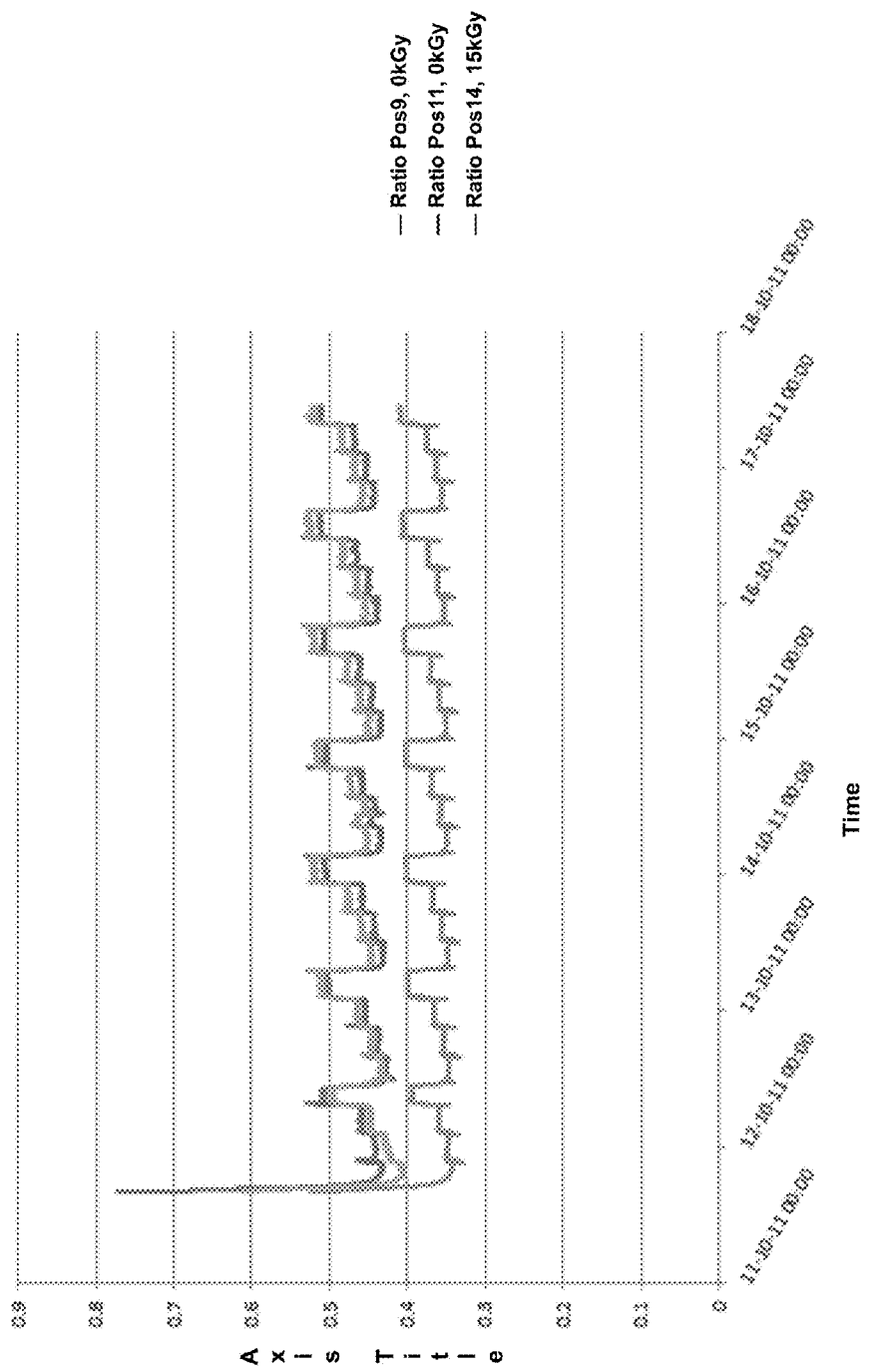
FIG. 3B provides a graph of data showing the startup of a freeze dried tubular capsule sensors comprising hygroscopic compound in an in vitro setup. The curves show the response from three dry sensors. As seen the sensor startup of the dry sensors is reduced to approximately 4 hours simply by adding two disaccharides to the composition of the sensor.
Figure 3C:
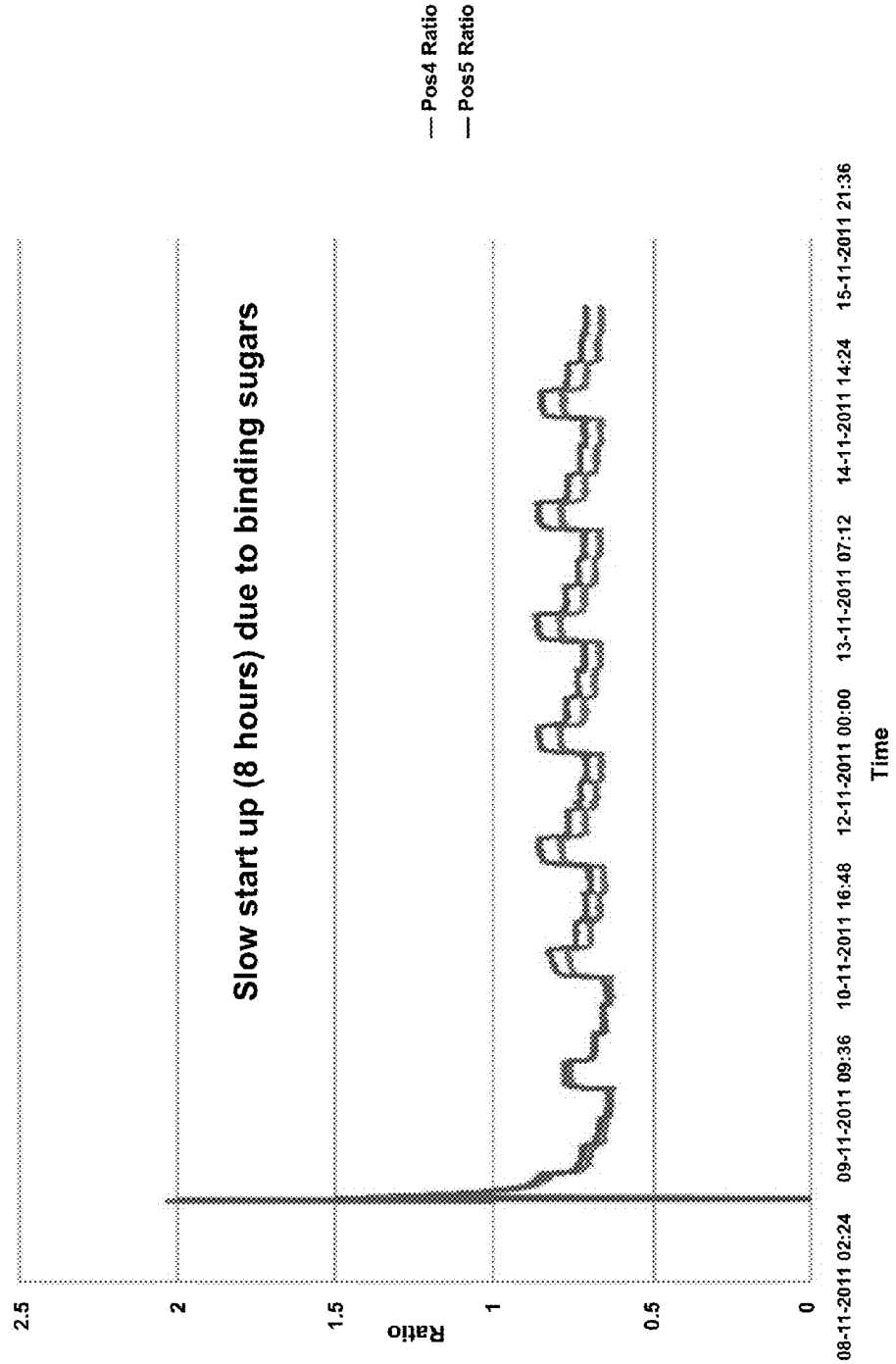
FIGS. 3C-3E provides graphs of data showing how specific combinations of different compositions can be used to modulate sensor startup times.
Figure 3D:
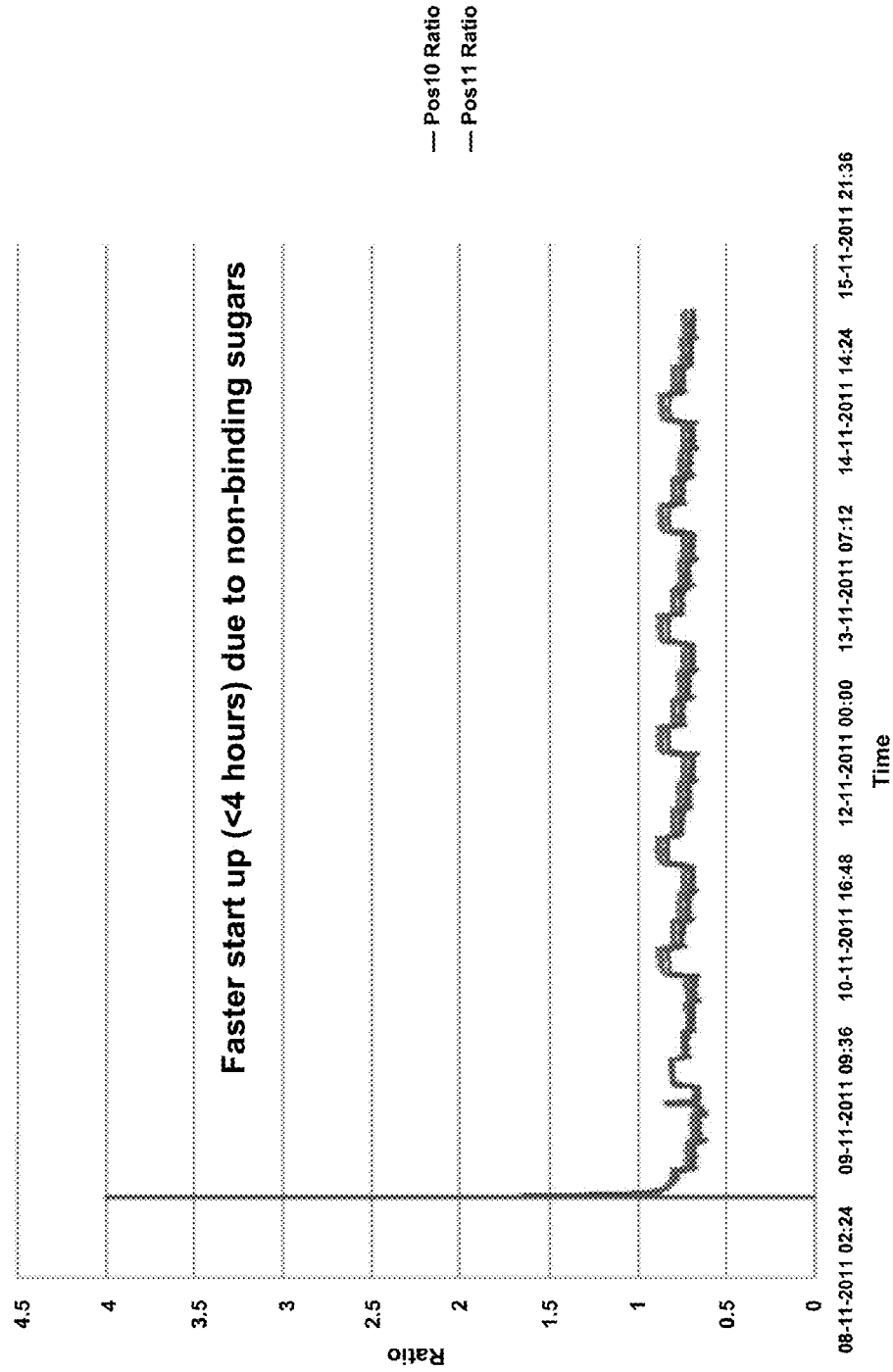
Figure 3E:
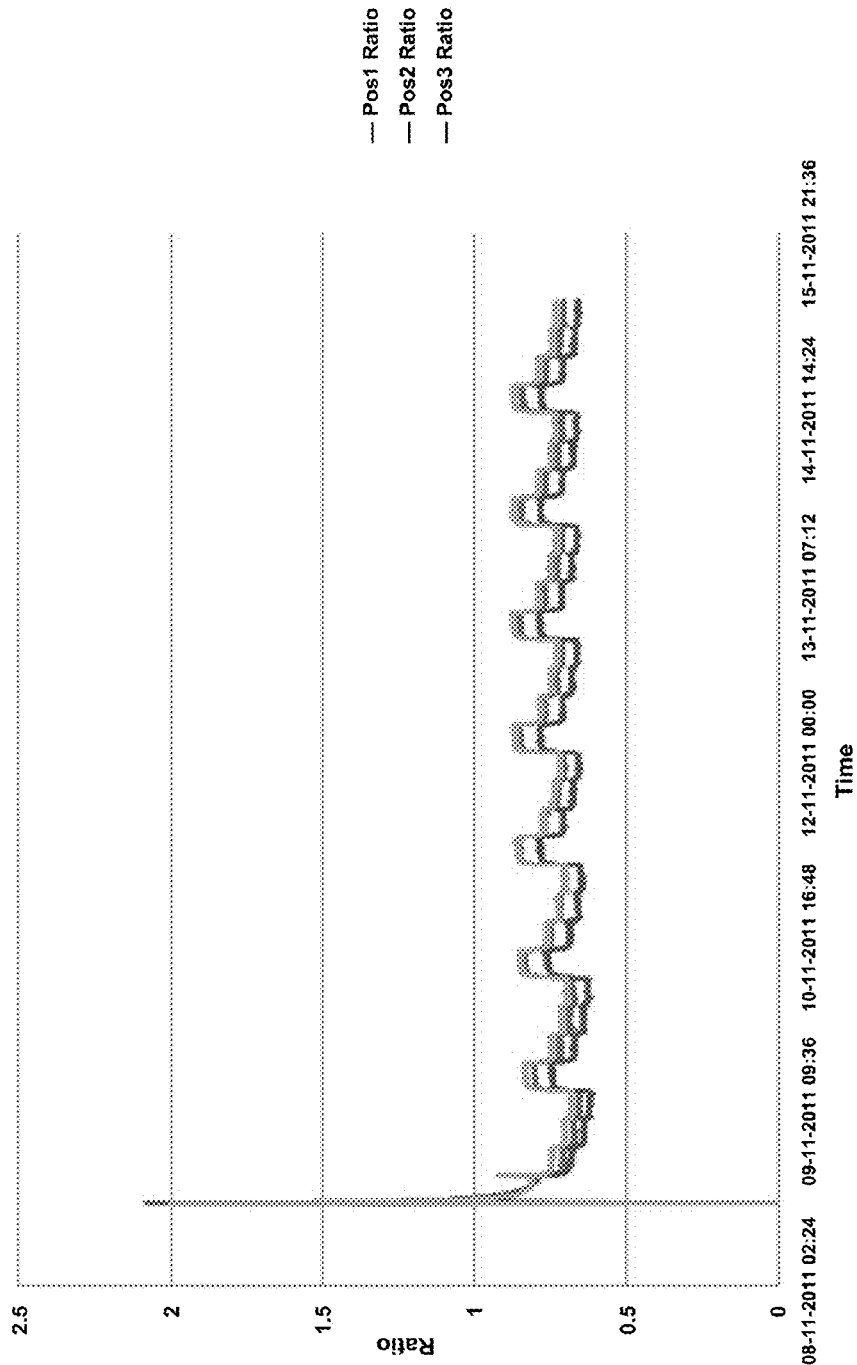

As shown in FIGS. 2-4, hygroscopic compounds such as saccharides (e.g. monosaccharides, disaccharides, trisaccharides, oligosaccharides and the like) as well as polyols (e.g. poly vinyl alcohols, mannitol, sorbitol and the like), polyethylene glycol (PEG) molecules of various molecular weights, as well as salts (e.g. NaCl, KCl and the like) can be used to greatly enhance the startup time of sensors. The data presented in FIGS. 3A and 3B shows that hygroscopic compositions can decrease the start-up time period for an illustrative sensor from 36 hours (i.e. the time period for a control sensor lacking these compositions) down to under 4 hours when the same sensor is formulated to comprise the hygroscopic compositions sucrose and trehalose.

The data presented in FIG. 3 shows that the addition of hygroscopic compositions can be use to modulate (typically to increase) startup time of the sensor. This shows for example, that disposing such compositions at particular sensor areas, for example, by forming a sensor matrix (one that is ultimately dried) to include hygroscopic compounds within a cavity/void in which a sensing complex (e.g. one comprising a binding assay) is also disposed helps to increase startup time. Different compositions can be used with different sensors in order to modulate conditions in specific ways. For example in some embodiments of the invention, osmotic pressure of the compositions used during the wetting can be modulated by using hygroscopic compounds which are selected for an ability to migrate from a site at which they were originally disposed by, for example, diffusing away from the site following sensor placement in an aqueous environment (e.g. by selecting low molecular weight saccharides that can diffuse through a polymeric matrix without being entrapped). Alternatively, hygroscopic compounds can be adapted or selected to remain in a specific area of a sensor for some extended period of time, for example by irreversibly coupling them to a fixed location, or by using a high molecular weight hygroscopic compounds they have difficulty diffusing through a polymeric matrix (e.g. polyols of selected molecular weights) and/or sugars having selected molecular weights etc. and, in this way, maintain an osmotic pressure at a location for a controlled period of time (e.g. to produce a faster startup time). Polymers useful for forming sensors of the invention include hydrogels, acrylates and the like (see, e.g. U.S. Patent Application Publication Nos. 20080188723, 20090221891, 20090187084 and 20090131773, the contents of each of which are incorporated herein by reference).

Embodiments of the invention include materials and methods for removing gases within a sensor (i.e. air, combinations of $O_2$ and $N_2$ and other minor constituents) as well as other gases (e.g. $N_2$, He or Ne gasses introduced into sensors and/or packaging due to their relatively inert nature and/or solubility profiles) from inside a wetted polymer structure by using osmotic forces generated by hygroscopic compositions, gas evolution to increase pressure and an efficient method to remove the evolved gas from gas phase to solvated phase at ambient pressure and body temperature. Embodiments of the invention exhibit functional profiles (e.g. quicker start-up times) that are highly desirable to those using such systems (e.g. diabetic patients who play an active role in monitoring physiological glucose concentrations). For example, in certain embodiments of the invention disclosed herein, the period of time between sensor contact with the aqueous environment (e.g. implantation in vivo) and generation of an observable analyte signal is less than 4, 3, 2 or 1 hours.

In this context, certain embodiments of the invention comprise compositions designed to force air out of the sensors. In an illustrative embodiment of one such sensor system, the sensor includes a gas evolving composition coupled to one or more regions of the sensor and adapted to generate a gas upon exposure to water (e.g. when the sensor is disposed within the aqueous environment) and in this way, displace the air so that it is forced out of the sensor. In certain embodiments of the invention disclosed herein, 90% of the air is forced out of the sensor in less than 4, 3, 2 or 1 hours following sensor exposure to an aqueous environment. As discussed below, typical embodiments of the invention, a gas evolving composition produces carbon dioxide. In some embodiments of the invention, a gas within the sensor, for example one introduced during manufacturing, is selected to have a relatively high solubility as compared to gases found in air (e.g. He, Ne and the like). In certain embodiments, one or more gases introduced into the sensor and/or produced by a gas evolving composition is elected for high solubility due to an equilibrium in water (e.g. $NH_3/NH_4+$) and/or an ability to form soluble compounds when exposed to an aqueous environments (optionally in combination with acidic or basic excipient compositions). A working embodiment of the invention that is disclosed herein uses bicarbonates (hydrogen carbonates) that are capable of liberating $CO_2$ gas under acidic conditions as gas evolving compositions. In this context, acidic conditions during the startup can be generated by adding acidic excipients in to the composition. Similarly, the presence of high concentrations of sugars or other hydroscopic compositions also change the activity coefficients solutions making them acidic (e.g. adding 0.5 M sucrose to a 50 mM Tris buffer pH 7.68 changes the pH to approx. 3.5 in the resulting solution). In view of this, certain embodiments of the invention use high sugar concentrations and bicarbonates to liberate $CO_2$ gas during wetting and hence increase the gas pressure inside the sensor. Optionally, a $CO_2$ gas generating composition comprises a compound selected from the group consisting of $NaHCO_3$, $Na_2CO_3$, $NH_4HCO_3$, $(NH_4)_2CO_3$, $KHCO_3$ and $K_2CO_3$. In certain embodiments of the invention, the sensors are sealed within gas impermeable packaging in order to, for example, inhibit any loss of $CO_2$ from such carbonates (and change the carbonate content).

After the generation of $CO_2$ gas, the dissolution of this $CO_2$ in to water is a relatively slow process. Consequently, merely exchanging $O_2$ and $N_2$ (i.e. air) with $CO_2$ does not necessarily help to increase startup time. Consequently, as disclosed herein, certain sensor system embodiments are adapted to include a gas evolving composition also include a composition adapted to sequester, solvate or otherwise remove the gas generated by the gas evolving composition. In this context a number of materials that sequester gases such as $CO_2$ are known in the art (see, e.g. Huang et al., Proc Natl Acad Sci 2011 108(4): 1222-1227). In addition, the slow process of dissolving $CO_2$ gas in water is in nature catalyzed by an enzyme Carbonic Anhydrase (CA) or carbonate dehydratase (EC 4.2.1.1). The carbonic anhydrases (or carbonate dehydratases) form a family of enzymes that catalyze the rapid interconversion of carbon dioxide and water to bicarbonate and protons (or vice versa), a reversible reaction that occurs rather slowly in the absence of a catalyst ($CO2+H20 \rightleftarrows H2CO3$). One of the functions of this enzyme in animals is to interconvert carbon dioxide and bicarbonate to maintain acid-base balance in blood and other tissues, and to help transport carbon dioxide out of tissues. The rate of conversion is diffusion controlled i.e. the fastest possible reaction is obtained by the presence of CA. CA is found in all higher organisms is all compartments. In laboratories the CA is commonly used to keep $CO_2/H_2CO_3$ equilibrium when working with mammalian cell lines (in $CO_2$ incubators). CA is readily available from SIGMA ALDRICH, for example as both bovine and human variants.

Formulating the sensor with CA, a disaccharide, monosaccharide and $HCO_3-$ yields a composition that can remove air relatively quickly as compared to a sensor containing only the hygroscopic compounds and/or gas evolving compositions. Results from control experiments shown in Table 1 below confirm that a hygroscopic composition, a gas evolving composition and CA can be use to obtain fast startup. The results from illustrative experiments are as follows:

TABLE 1

| Composition of composition | 90% air removal |
|---|---|
| 0.5M Sucrose + CA | >4 hour |
| 0.5M Sucrose + 0.2M $NaHCO_3$ | >4 hours |
| 0.2M $NaHCO_3$ + CA | >10 hours |
| 0.5M Sucrose + 0.2M $NaHCO_3$ + CA | 30 minutes |

As shown above, by incorporating a composition comprising 0.5 M disaccharide, 0.5 M monosaccharide and 0.2 M $HCO_3-$ and excess of CA inside of a representative sensor, 90% of air is removed in approximately 30 minutes. As shown in FIG. 4, using such information, artisans can make optimized concentrations for a variety of sensors and/or use an optimized combination of compositions (such as di- and monosaccharides) for a desired application, for example an optimal bicarbonate concentration needed to keep the reactions proceeding at a desired rate until all air is removed. Ways to optimize the rate of hydration and/or the air removal in various sensor structures include the three dimensional placement and/or distribution of the compositions within a sensor structure, for example to drive fluids in a specific direction or generate (or solvate) gas in a specific location (e.g. towards a sensing complex) etc. As discussed below, depending upon the nature of the sensor in which embodiments of the sensor are used, additional ways to optimize the rate of hydration and/or the air removal in various sensor structures include, for example: (1) controlling pH during startup in order to optimize the gas evolution; (2) varying the concentrations of the various compositions; (3) selecting specific combinations of compositions, for example combining highly soluble compounds (fast dissolution) with compounds having lower solubility (slower dissolution); and (4) selecting the specific site (e.g. an internal cavity) and manner in which such compositions are disposed within the sensor (e.g. to make them diffuse away from the site a specific rate or, to entrap them at that site etc.). For example, as is known in the art, higher concentrations of excipients can produce higher osmotic pressures and hence the faster the air removal. Other factors relating to the mechanisms of the invention can be considered as well. For example, some embodiments of the invention are designed so that the "osmolality" of the compositions is in a concentration range from 2M to 4M in total including a disaccharide, a mono saccharide and a bicarbonate.

As noted above, in an illustrative embodiment of the invention, the gas generated is carbon dioxide and the sensor system includes a carbonic anhydrase composition coupled to one or more regions of the sensor. In such embodiments, the carbonic anhydrase converts the carbon dioxide gas into soluble bicarbonates and protons that subsequently diffuse out of the sensor and into the aqueous environment. As disclosed herein, the sensor systems of embodiments of the invention can include a number of other compositions, for example those which can modulate sensor characteristics including those discussed above such as hydration, gas generation and/or gas removal. In some embodiments of the invention, the sensor comprises a composition that forms an acidic excipient or a basic excipient coupled to one or more regions of the sensor and adapted to modulate the pH within the sensor when the sensor is disposed within the aqueous environment. "Acidic excipient" as that term is used herein refers to any organic acid. These excipients can be added as the acid, or as the salt form of the conjugate base of the acid. For example, the acidic excipient citric acid can be added either in the acid form, citric acid, or as the salt form of the conjugate base, for example, the mono-, di-, or trisodium salt of the citric acid. Illustrative acidic excipients include citric acid, ascorbic acid, acetic acid, ethylenediaminetetra acetic acid, saturated fatty acids, bile acids, dicarboxylic acids, and combinations thereof. Illustrative basic excipients include a number of inorganic or organic bases which are physiologically harmless, that is, pharmaceutically acceptable, at least in the dosage ranges used, such as sodium hydroxide, potassium hydroxide, ammonia, tert.-sodium phosphate, diethanolamine, ethylenediamine, N-methylglucamine or L-lysine.

As disclosed herein, the sensor can also include a variety of other compounds such as surfactants (e.g. Tween-80, Triton X100 used in the working examples). These can be anionic, cationic, nonionic, and Zwitterionic surfactants. In some embodiments of the invention, the sensor comprises a colloid composition selected to increase the solubility of a gas generated by a gas generating composition. In certain embodiments of the invention, the sensor comprises a convection composition coupled to one or more regions of the sensor and adapted to generate convection within the sensor when the sensor is disposed within the aqueous environment.

As disclosed for example in FIG. 4, various combinations of compositions can be used in embodiments of this invention (e.g. those including Sucrose+NaHCO3+CA), combinations which can be selected in view of the specific sensor structures in which they are used as well the specific functional effect that is desired for that sensor. With embodiments of the tubular capsule sensors that are shown in FIGS. 1 and 2, where fast hydration and air removal is desired, it is observed that embodiments work well with combinations of monosaccharides and disaccharides when one sugar is selected to be highly soluble (see, e.g. Sucrose>Lactose>Trehalose and related solubility comparisons). In situations where sensors comprise an internal cavity that includes a solubilizable sensor complex, a complex/assay distributed on entire inside surface of the sensor cavity in order to provide selected results. Sucrose (or glucose) are highly soluble sugars that contribute to ensure wetting and dissolution/distribution of the assay inside the sensor cavity (and raise the osmotic pressure). PVAs of various molecular weights (e.g. 6 kDa or 195 kDa etc.) can also be employed to decrease the time for air removal.

The compositions used in embodiments of the invention exhibit a surprising degree of flexibility and versatility, characteristics which allow them to be adapted for use in a wide variety of sensor structures. In this context, embodiments of the invention can use sensors and/or sensor elements selected to have shapes and sizes and materials that influence diffusion through the sensor. For example, in some embodiments of the invention, the sensor is designed to have a geometry that facilitates in vivo placement and analyte diffusion into the sensor, and is, for example spherical, ellipsoid, tubular or the like. In certain embodiments of an invention the size of the sensor is kept below a minimum size in order to facilitate the diffusion of compounds therethrough. In some embodiments of the invention, one or more sensor elements can comprise a structure formed from a polymeric composition through which water and other compounds such as analytes (e.g. glucose) can diffuse. Illustrative polymeric compositions are disclosed in U.S. Patent Publication No. 20090221891 and include, for example, material (e.g. one that is biodegradable) comprising a polymer having hydrophobic and hydrophilic units. Specific polymers can be selected depending upon a desired application. For example, for mobility of glucose, a material can be selected to have a molecular weight cut-off limit of no more than 25000 Da or no more than 10000 Da. Components disposed within such polymeric materials (e.g. sensing complexes) can be of high molecular weight, for example proteins or polymers, in order to prevent their loss from the sensor by diffusion through the polymeric materials. In an illustrative embodiment, hydrophilic units of a polymeric material comprise an ester of polyethylene glycol (PEG) and a diacid, and the molecular weight cut-off limit is affected by the PEG chain length, the molecular weight of the polymer and the weight fraction of the hydrophilic units. The longer the PEG chains, the higher the molecular weight cut-off limit, the higher the molecular weight of the polymer, the lower the molecular weight cut-off limit, and the lower the weight fraction of the hydrophilic units, the lower the molecular weight cut-off limit.

Sensor components can be selected to have properties that facilitate their storage and or sterilization. In some embodiments of the invention, all components of the sensor are selected for an ability to retain sensor function following a sterilization procedure (e.g. e-beam sterilization). In some embodiments of the invention, all components of the sensor are selected for an ability to retain sensor function following a drying procedure (e.g. lyophilization).

In illustrative embodiments of the invention, the sensor comprises a cylindrical/tubular architecture and has a diameter of less than 1 mm, 0.9 mm, 0.8 mm, 0.7 mm, 0.6 mm, 0.5 mm, 0.4 mm, 0.3 mm or 0.2 mm. Illustrative sensors of this type are shown in FIG. 1. In certain examples, the sensor has a diameter of about 0.5 mm or about 0.25 mm. In some embodiments, the body of sensor is formed from a polymeric material. Optionally, the sensor is in the form of a fiber. In some embodiments of the invention, the internal matrix of a cylindrical sensor comprises one or more cavities or voids, for example a encapsulated longitudinal cavity. In certain embodiments of the invention, the sensing complex, the hygroscopic composition, the gas evolving composition, the composition adapted to sequester, remove, solvate etc., the gas generated by the gas evolving composition, the convection composition and/or the pH modulating composition is disposed in the one or more of these cavities/voids.

Optionally the sensing complex produces an optical signal that can be correlated with an analyte of interest, for example, glucose. A sensing complex (e.g. one comprising a binding assay) generating the optical signal should preferably be reversible such that a continuous monitoring of fluctuating levels of analyte can be achieved. Optionally, the detectable or measurable optical signal is generated using a proximity based signal generating/modulating moiety pair so that a signal is generated or modulated when a first member of the pair is brought into close proximity with a second member of the pair. In one illustrative embodiment, the analyte binding agent (e.g. a lectin such as mannose binding lectin as disclosed in WO 2006/061207) is labelled with one of a proximity based signal generating/modulating moiety pair and the analyte analogue is labelled with the other of the proximity based signal generating/modulating moiety pair, and there is a detectable difference in signal when the analyte analogue and analyte binding agent form the complex and when the analyte analogue is displaced by the analyte from the complex. Typically, the proximity based signal generating/modulating moiety pair is an energy donor moiety and energy acceptor moiety pair. Energy donor moieties and energy acceptor moieties are also referred to as donor and acceptor chromophores (or light absorbing materials) respectively. An energy acceptor which does not emit fluorescence is referred to as a quenching moiety. In such embodiments, a lectin can be labelled with one of an energy donor and energy acceptor moiety pair and the analyte analogue is labelled with the other of the energy donor and energy acceptor moiety pair. The detectable difference in signal corresponds to a detectable difference in energy transfer from the energy donor moiety to the energy acceptor moiety. Optionally, the analyte analogue bears the energy acceptor moiety and the analyte binding agent bears the energy donor moiety. In certain embodiments of the invention, the sensor of the invention incorporates an assay which generates an optical readout using the technique of fluorescence resonance energy transfer (FRET).

In one illustrative embodiment of the sensors discussed in the paragraph above, the variants of the competitive binding assay each comprise: an analyte binding agent labelled with a first light-absorbing material; a macromolecule labelled with a second light-absorbing material and comprising at least one analyte analogue moiety; wherein the analyte binding agent binds said at least one analyte analogue moiety of the macromolecule to form a complex from which said macromolecule is displaceable by said analyte, and wherein said complex is able to absorb light energy and said absorbed light energy is able to be non-radiatively transferred between one of the light-absorbing materials and the other of the light-absorbing materials with a consequent measurable change in a fluorescence property of said light absorbing materials when present in said complex as compared to their said fluorescence property when said macromolecule is displaced by said analyte from said complex, and wherein the different variants of the assay are distinguished by the number of analyte analogue moieties present in the macromolecule. Such sensors are disclosed, for example in U.S. Patent Application Publication Nos. 20080188723, 20090221891, 20090187084 and 20090131773, the contents of each of which are incorporated herein by reference.

Figure 1D:
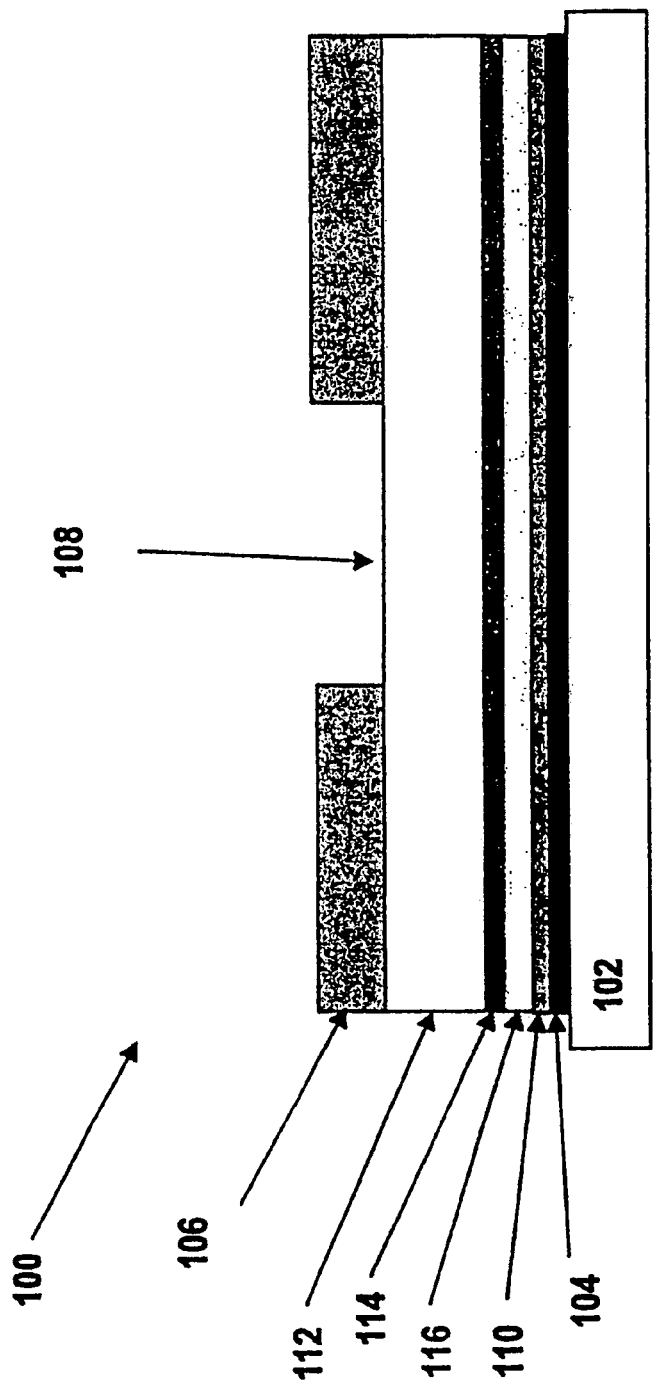
FIG. 1D shows a diagram of shows an alternative sensor design, one comprising an amperometric analyte sensor formed from a plurality of planar layered elements.
Figure 5:
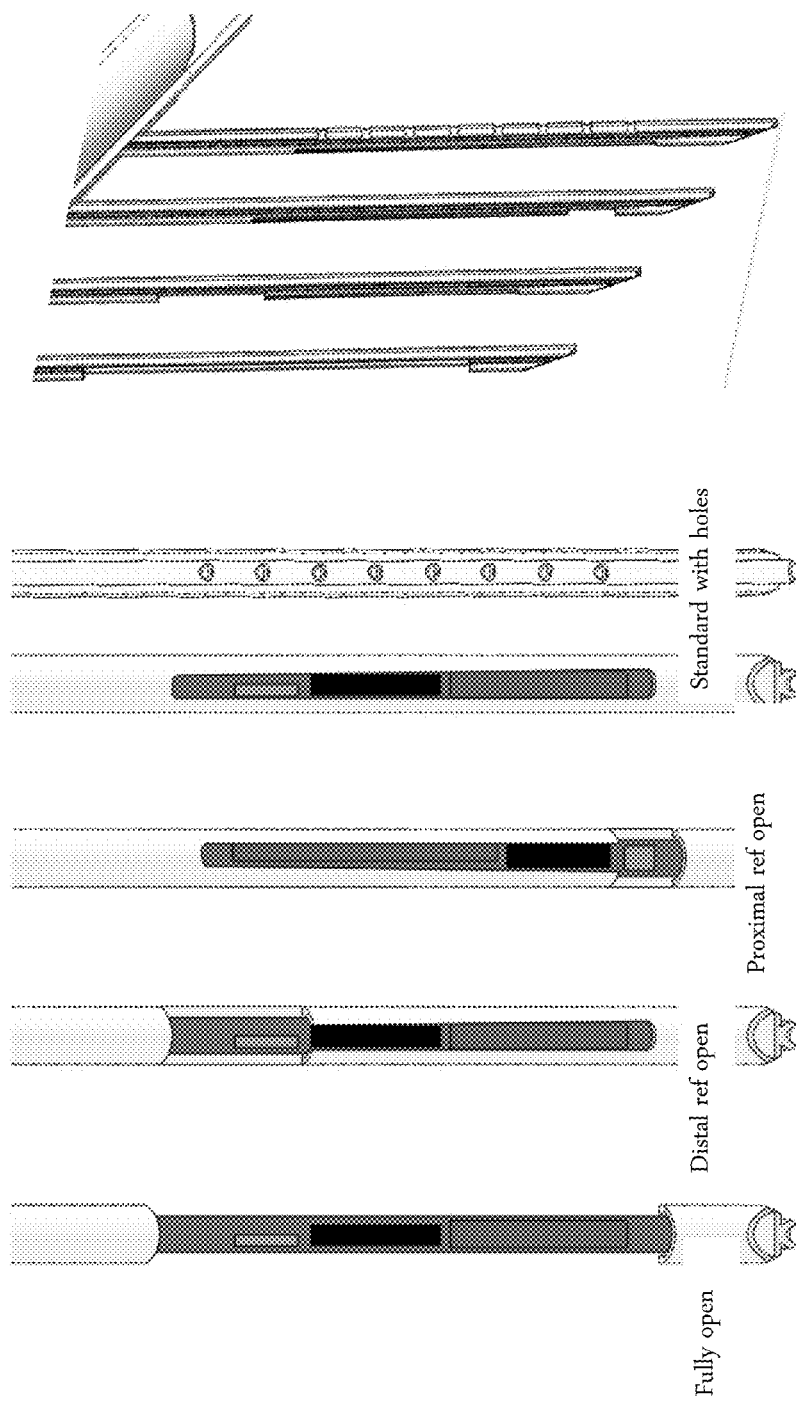
FIG. 5 provides a diagram of amperometric sensor systems having various configurations. As illustrated by this figure, in certain embodiments of the invention, the sensor is disposed within tubular housing (e.g. a lumen of a catheter). In some embodiments of the invention, the hygroscopic composition coats a region of this housing. The rectangles observed through these apertures are working, reference and counter electrodes. In some embodiments of the invention, the hygroscopic composition is disposed in a layer of material coated over an electrode.

In other embodiments of the invention, the sensor comprises planar layered elements and, for example comprises a conductive layer including an electrode, an analyte sensing layer disposed over the conductive layer (e.g. one comprising glucose oxidase); and an analyte modulating layer disposed over the analyte sensing layer. In some embodiments of the invention, the hygroscopic composition is disposed within a planar layer (e.g. entrapped within a polymer of the layer), for example in the analyte sensing layer or the analyte modulating layer. In certain embodiments of the invention, the sensor electrode is disposed within a housing (e.g. a lumen of a catheter) and the hygroscopic composition coats a region of the housing. Illustrative embodiments of this nature are shown in FIG. 5. In one illustrative embodiment of the invention, the hygroscopic composition is entrapped within a polymeric composition disposed on an inner wall of a catheter. In another illustrative embodiment of the invention, the hygroscopic composition is entrapped within a composition disposed over a sensor electrode The sensor embodiment shown in FIG. 1D is a amperometric sensor 100 having a plurality of layered elements including a base layer 102, a conductive layer 104 which is disposed on and/or combined with the base layer 102. Typically the conductive layer 104 comprises one or more electrodes. An analyte sensing layer 110 (typically comprising an enzyme such as glucose oxidase) is disposed on one or more of the exposed electrodes of the conductive layer 104. A protein layer 116 disposed upon the analyte sensing layer 110. An analyte modulating layer 112 is disposed above the analyte sensing layer 110 to regulate analyte (e.g. glucose) access with the analyte sensing layer 110. An adhesion promoter layer 114 is disposed between layers such as the analyte modulating layer 112 and the analyte sensing layer 110 as shown in FIG. 1D in order to facilitate their contact and/or adhesion. This embodiment also comprises a cover layer 106 such as a polymer coating can be disposed on portions of the sensor 100. Apertures 108 can be formed in one or more layers of such sensors. Amperometric glucose sensors having this type of design are disclosed, for example are disclosed, for example, in U.S. Patent Application Publication Nos. 20070227907, 20100025238, 20110319734 and 20110152654, the contents of each of which are incorporated herein by reference.

In many embodiments of the invention, the sensors comprise a biocompatible region adapted to be implanted in vivo. In some embodiments the whole sensor is adapted to be implanted in vivo. In other embodiments, the sensor comprises a discreet probe that pierces an in vivo environment. In embodiments of the invention, the biocompatible region can comprise a polymer that contacts an in vivo tissue. Optionally, the polymer is a hydrophilic polymer (e.g. one that absorbs water). In this way, sensors used in the systems of the invention can be used to sense a wide variety of analytes in different aqueous environments. In common embodiments of the invention, the sensing complex is adapted to sense glucose.

A related embodiment of the invention is a method for making a sensor having properties that allow it to modulate a time period between placement of a sensor within an aqueous environment and generation of a sensor signal that can be correlated with the concentration of a sensed analyte. Typically the method comprises forming the sensor to have an exterior surface and an internal matrix comprising at least one sensing complex adapted to sense analytes within aqueous environments; and a hygroscopic composition coupled to one or more regions of the sensor so as to modulate the rate of hydration of the sensing complex when the sensor is disposed within the aqueous environment (e.g. to increase the rate of hydration as compared to a control sensor that lacks the hygroscopic composition). In such methods, the specific compounds used, their concentrations and positional placement of the hygroscopic composition(s) within the sensors during their manufacture can be used to modulate the time period between: (1) sensor placement in the aqueous environment; and (2) generation of a sensor signal that can be correlated with the concentration of the analyte.

Certain methodological embodiments of the invention comprise a method for making a sensor having properties that allow it to force air out the internal matrix of the sensor, for example, by forming the sensor to comprise a gas evolving composition coupled to one or more regions of the sensor, wherein the gas evolving composition is adapted to form carbon dioxide when the sensor is disposed within the aqueous environment, thereby forcing air out of the internal matrix of the sensor. Typically these methods include making a sensor that can remove carbon dioxide atoms generated when the sensor is disposed within the aqueous environment by, for example, forming the sensor to comprise carbonic anhydrase which can convert the carbon dioxide into bicarbonate that will diffuse out of the sensor into the aqueous environment. Some methodological embodiments of the invention comprise making the sensor to include compositions having other desirable properties. For example, in some embodiments, the method comprises making a sensor having properties that allow it to generate convection within the internal matrix of the sensor by forming the sensor to include a convection composition (e.g. so as to facilitate mixing of other sensor constituents). In addition, in some embodiments, the method comprises making a sensor which can modulate the internal pH of the sensor, for example, by forming the sensor to include compositions that modulate the pH of aqueous environments (e.g. buffering compounds, acidic and basic compounds and the like).

Yet another embodiment of the invention is a method of sensing an analyte (e.g. glucose) within the body of a mammal, the method comprising implanting an analyte sensor system disclosed herein in to the mammal and then sensing a signal (e.g. an optical signal, a electrical signal or the like), and correlating the signal with the presence of the analyte, so that the analyte is sensed.

Methodological embodiments of the invention can be used with sensors having a variety of configurations and/or sensing complexes. In certain methodological embodiments of the invention, the sensor comprises a cylindrical polymeric material having a diameter of less than 1 mm, less than 0.5 mm or less than 0.25 mm, the internal matrix comprises an encapsulated longitudinal cavity, and the sensing complex comprises a carbohydrate binding lectin (e.g. mannose binding lectin which binds glucose) coupled to a fluorophore pair. In other methodological embodiments of the invention, the sensor comprises an electrode coated with glucose oxidase and a glucose limiting membrane disposed over the glucose oxidase, wherein the glucose limiting membrane modulates the diffusion of glucose therethrough. In addition, methods of the invention can be performed in a variety of environments under conditions selected to be appropriate for a selected environment. For example, in certain embodiments of the invention, the aqueous environment comprises an in vivo tissue and the method is performed at atmospheric pressure and at a temperature between 36 and 38 degrees centigrade.

Embodiments of the invention also provide articles of manufacture and kits for observing a concentration of an analyte. In an illustrative embodiment, the kit includes a sensor comprising an exterior surface and an internal matrix comprising at least one sensing complex adapted to sense analytes within aqueous environments and one or more hygroscopic compositions. In illustrative embodiments of the invention, the hygroscopic composition can comprise a saccharide compound (e.g., a monosaccharide, a disaccharide, a trisaccharide, an oligosaccharide) and/or a polyol such as a polyvinyl alcohol or a polyethylene glycol) and/or a salt (e.g. a salt used in pharmaceutical compositions). Optionally the sensor includes one or more gas (e.g. carbon dioxide) evolving composition in combination with one or more gas removing compositions. In illustrative embodiments of the invention, the gas evolving composition comprises a compound selected from the group consisting of $NaHCO_3$, $Na_2CO_3$, $NH_4HCO_3$, $(NH_4)_2CO_3$, $KHCO_3$ and $K_2CO_3$, and the carbon dioxide gas removing composition comprises an composition selected from the group consisting of carbonic anhydrase and carbonic anhydrase analogues (see, e.g. Bergquist et al., J. Am. Chem. Soc., 2003, 125 (20), pp 6189-6199). In some embodiments, the sensing complex comprises a carbohydrate binding lectin coupled to a fluorophore. Alternatively, the sensing complex comprises an electrode coated with a glucose oxidase composition. In typical embodiments, the sensors are disposed in the kit within a sealed sterile dry package.

Optionally the kit comprises an insertion device that facilitates insertion of the sensor. The kit and/or sensor set typically comprises a container, a label and an analyte sensor as described above. Suitable containers include, for example, an easy to open package made from a material such as a metal foil, bottles, vials, syringes, and test tubes. The containers may be formed from a variety of materials such as metals (e.g. foils) paper products, glass or plastic. The label on, or associated with, the container indicates that the sensor is used for assaying the analyte of choice. The kit and/or sensor set may include other materials desirable from a commercial and user standpoint, including buffers, diluents, filters, needles, syringes, and package inserts with instructions for use.

Various publication citations are referenced throughout the specification. The disclosures of all citations in the specification are expressly incorporated herein by reference. All numbers recited in the specification and associated claims that refer to values that can be numerically characterized can be modified by the term "about".

The invention claimed is:

1. A method for decreasing a waiting time between placement of a sensor within an aqueous environment comprising an in vivo tissue and generation of a sensor signal that can be correlated with the concentration of a sensed analyte, the method comprising:
    (a) selecting the sensor to be configured as a cylindrical fiber formed from a biocompatible polymeric material having a diameter of less than 1 mm and having an encapsulated longitudinal cavity disposed therein:
        (i) an exterior surface and an internal matrix within the cavity comprising air and at least one sensing complex that senses analytes within aqueous environments;
        (ii) a hygroscopic composition disposed on a surface within the cavity; and
        (iii) carbonic anhydrase disposed on a surface within the cavity; and
    (b) placing the sensor into an aqueous environment that comprises an in vivo tissue;
    (c) allowing the hygroscopic composition to modulate hydration of the sensing complex; and
    (d) generating a sensor signal that can be correlated with the concentration of the analyte following said hydration of the sensing complex; wherein:
    a waiting time between sensor placement in the aqueous environment and generation of a sensor signal that can be correlated with the concentration of the analyte is decreased by steps (a)-(d).

2. The method of claim 1, wherein the hygroscopic composition comprises a salt and a saccharide.

3. The method of claim 1, wherein the hygroscopic composition comprises a saccharide and a polyol.

4. The method of claim 1, wherein the hygroscopic composition comprises a saccharide, a polyol and a salt.

5. A method for decreasing a waiting time between placement of a glucose sensor within an aqueous environment comprising an in vivo tissue and generation of a sensor signal that is correlated with the concentration of glucose, the method comprising:
    (a) selecting the sensor to be configured as a cylindrical fiber having a diameter of less than 1 mm and formed from a biocompatible polymeric material that allows the diffusion of glucose therethrough, wherein the cylindrical fiber:
        (i) comprises an exterior sensor surface that contacts the aqueous environment comprising glucose; and
        (ii) comprises an encapsulated longitudinal cavity having an internal surface with the following disposed thereon:
            a sensing complex comprising a mannose binding lectin, wherein the sensing complex senses glucose that has diffused from the aqueous environment through the biocompatible polymeric material and into the encapsulated longitudinal cavity;
            a hygroscopic composition; and
            carbonic anhydrase; and
    (b) placing the sensor into an aqueous environment that comprises glucose;
    (c) allowing the hygroscopic composition to modulate hydration of the sensing complex; and
    (d) generating a sensor signal that is correlated with the concentration of glucose following said hydration of the sensing complex; wherein:
    a waiting time between sensor placement in the aqueous environment and generation of a sensor signal that can be correlated with the concentration of glucose is decreased by steps (a)-(d).

6. The method of claim 5, wherein the hygroscopic composition comprises a saccharide.

7. The method of claim 6, wherein the hygroscopic composition comprises sucrose.

8. The method of claim 7, wherein the hygroscopic composition further comprises a polyol.

9. The method of claim 8, wherein the hygroscopic composition further comprises a salt.

10. The method of claim 5, wherein the sensing complex further comprises a fluorophore.

11. The method of claim 5, wherein the hygroscopic composition is irreversibly coupled to a fixed location within the cavity.

12. The method of claim 5, wherein the cavity further comprises at least one compound selected from the group consisting of $NaHCO_3$, $Na_2CO_3$, $NH_4HCO_3$, $(NH_4)_2CO_3$, $KHCO_3$ and $K_2CO_3$.

13. The method of claim 5, wherein the cavity further comprises an acidic excipient.

14. The method of claim 13, wherein the acidic excipient is citric acid.

* * * * *